US00PP37412P2

(12) United States Plant Patent
Raywood

(10) Patent No.: US PP37,412 P2
(45) Date of Patent: May 5, 2026

(54) ***FESTUCA* PLANT NAMED 'Perfect Edging'**

(50) Latin Name: ***Festuca arundinacea* (Schreb.); *(Lolium arundinacea* (Schreb.) Darbysh.)**
Varietal Denomination: Perfect Edging

(71) Applicant: Michael Raywood, Parkesburg, PA (US)

(72) Inventor: Michael Raywood, Parkesburg, PA (US)

( * ) Notice: Subject to any disclaimer, the term of this patent is extended or adjusted under 35 U.S.C. 154(b) by 0 days.

(21) Appl. No.: 18/831,768

(22) Filed: Aug. 19, 2025

(51) Int. Cl.
*A01H 6/46* (2018.01)
*A01H 5/12* (2018.01)

(52) U.S. Cl.
USPC ..... Plt./384

(58) Field of Classification Search
USPC ..... Plt./384
CPC ..... A01H 6/46; A01H 5/12
See application file for complete search history.

*Primary Examiner* — Keith O. Robinson

(57) ABSTRACT

The new and distinct cultivar of ornamental, winter-hardy, blue fescue plant, *Festuca arundinacea* 'Perfect Edging', with highly vigorous, clumps of tight, full, rounded habit of strong stems and foliage, and mostly upright panicles. The foliage is variegated with creamy margins and dark green centers.

2 Drawing Sheets

Botanical classification: *Festuca arundinacea* (Schreb.); (*Lolium arundinacea* (Schreb.) Darbysh.).
Variety denomination: 'Perfect Edging'.

BACKGROUND OF THE INVENTION

The present invention relates to a new and distinct plant of blue fescue, botanically known as *Festuca arundinacea* 'Perfect Edging' and will be referred to hereinafter also by solely its cultivar name, 'Perfect Edging' and the "new plant."

*Festuca* 'Perfect Edging' was discovered by the inventor as a whole plant mutation of an unnamed Tall Fescue, *Festuca arundinacea*, at a private garden in Parkesburg, Pennsylvania. Evaluations were performed in a full-sun trial garden at the same garden and the new plant was subsequently assigned the cultivar name 'Perfect Edging'. The plant was propagated by division at the same private garden as early as 2019. The resultant asexually propagated divisions have been stable and identical to the original plant in successive asexual propagations.

No plants of *Festuca* 'Perfect Edging' have been offered for sale or sold in this country or anywhere in the world under this or any other name prior to the filing of this application, nor has any disclosure of the new plant been made more than one year prior to the filing of this application.

SUMMARY OF THE INVENTION

*Festuca arundinacea* 'Perfect Edging' differs from its parent as well as all other Tall Fescue known to the inventor in a combination of traits. The following characteristics in combination distinguish 'Perfect Edging' from all other blue fescue plants known to the inventor:

1. Tight, full, rounded foliage habit with mostly upright flower panicles;
2. Foliage is variegated with creamy margins with dark green centers;
3. Highly vigorous clumps.

The nearest comparison plants known to the inventor are the seed parent plant, *Festuca arundinacea* 'Glow Sticks' U.S. Plant Pat. No. 34,648, *Festuca glauca* 'Casca11' U.S. Plant Pat. No. 23,307, and *Festuca glauca* 'Elijah Blue' (not patented).

Compared to the parent, the new cultivar has leaves that are variegated with creamy margins and dark green centers, and the parent has leaves that are dark green without creamy margins. Compared with 'Glow Sticks' is taller in foliage and panicles and the foliage is dark green with a subtle central white stripe. Compared to 'Elijah Blue' the new plant is taller and wider in habit, more vigorous with broader variegated leaves. Compared to the cultivar 'Casca11' the new plant is taller and wider in habit, more vigorous with broader, less bluish, variegated leaves.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
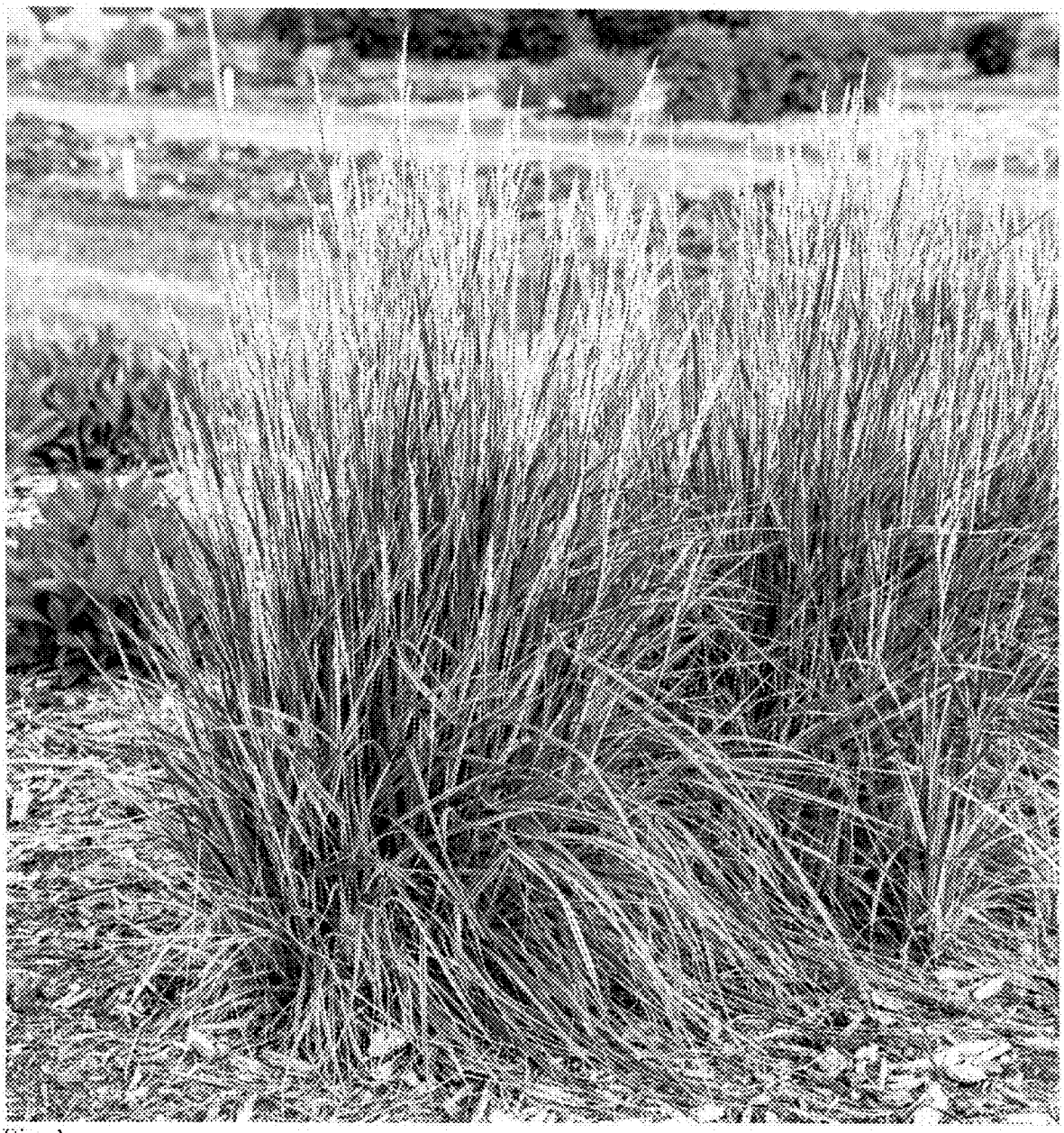
FIG. 1 shows a three-year-old plant of 'Perfect Edging' in the landscape in early flower.
Figure 2:
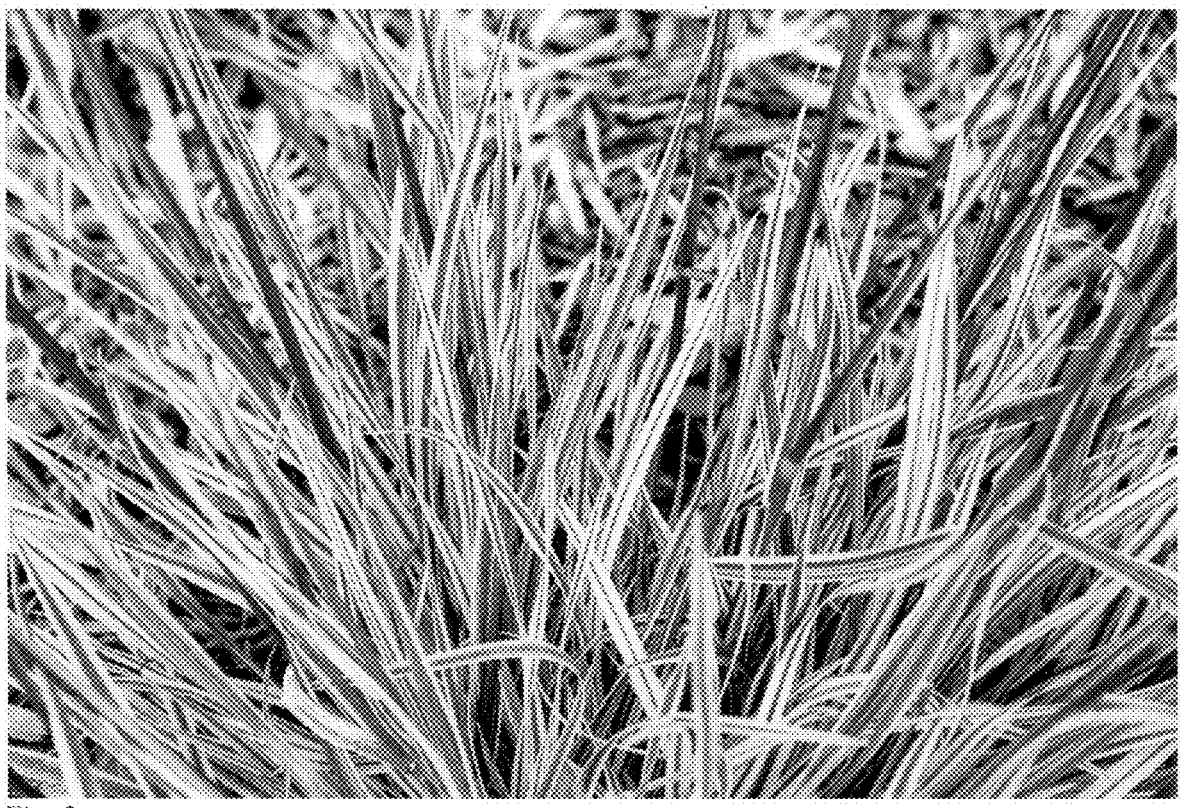
FIG. 2 shows a close-up of the young foliage with variegation.

The following is a detailed description of *Festuca* 'Perfect Edging' as observed in a display garden at a nursery in Zeeland, MI. The following description is of a two-year-old plant of 'Perfect Edging' in a full-sun display garden in Zeeland, Michigan with limited supplemental fertilizer and irrigation as needed and without any pinching or plant growth regulators. The new plant has not been observed under all possible environments, and the phenotype may vary slightly with different environmental conditions, such as temperature, light, fertility, moisture and maturity levels, but without any change in the genotype. The color descriptions are in accordance with the 2015 edition of The R.H.S. Colour Chart of The Royal Horticultural Society, London, England, except where common dictionary color terms are used.

Plant habit: Winter-hardy herbaceous perennial with dense mounded habit;

Plant size: Foliage to about 46 cm tall, 72 cm across; with about 30 flowering stems to about 64 cm tall, average about 42 cm tall;

Root description: Fibrous; color nearest RHS 155D;

Propagation: Division; finishing in 3-liter container in about 3 months during summer production;

Growth rate: Vigorous;

Crop time: Finishing in 3-liter container from a division in about 3 months during summer production;

Shoots and branches: Plant shoots developing from base with no branches; about 50 flowering shoots per plant;

Leaves: Linear, slightly arching; flat; apex narrowly acute; base decurrent, sheathed; margin entire; adaxial and abaxial glabrous and slightly lustrous; about four leaves per shoot; deciduous in Zeeland, MI;

Leaf blade size: To about 23 cm long and 11 mm across, average about 14.5 cm long and 8 mm across; margin variegation on young emerging leaves adaxial and abaxial to about 3 mm across, on mature mid-summer leaves to about 0.05 mm across adaxial and abaxial;

Leaf color: Young emerging leaves adaxial and abaxial margin between RHS 4D and RHS 11C, adaxial and abaxial center nearest RHS 137A; older leaves adaxial margin nearest RHS 155D and abaxial margin nearest RHS 157C, older leaves adaxial center and abaxial nearest RHS NN137B;

Sheath: About 12 cm long and 10 mm across, tightly enclosing culm; average 8.8 cm long and 8 mm across; color nearest RHS 137A with thin 0.5 mm wide stripes nearest RHS 155D;

Venation: Parallel; glabrous;

Vein color: Same as surrounding leaf tissue adaxial and abaxial; adaxial margin nearest RHS 155D and center nearest RHS NN137B, abaxial margin nearest RHS 157C and center nearest RHS NN137B;

Internode length: Covered with sheath; average about 11.4 cm;

Nodes: Swollen to about 4 mm across and 2.5 mm tall; color nearest RHS 146B;

Culm: Cylindrical; pithy; to about 58 mm long; aspect upright to slightly outwardly;

Culm color: Where exposed nearest RHS NN137B, where wrapped with sheath between RHS 145C and RHS 146D;

Ligule: Short; truncate; less than 0.3 mm long; membranous; color nearest RHS 200C;

Inflorescence: Panicle; to about 17 cm long;

Flowering season: Medium season; typically, in June into July; effective into fall;

Rachis: Cylindrical; smooth; glabrous; stiff; aspect upright;

Rachis color: Between RHS 189A and RHS NN137B when in flower, drying to nearest RHS 195A;

Pedicel: Cylindrical, thin, stiff; about 1 mm long and 0.5 mm diameter;

Pedicel color: Nearest RHS 138A;

Spikelet: With 3 to 6 flowers; to about 7 mm long, about 2.5 mm wide and about 1.5 mm thick;

Rachilla: Cylindrical; stiff; glabrous; to about 6 mm long and 0.3 mm diameter; color between RHS 138A and RHS N138A when in flower, drying to nearest RHS 195A;

Awn: Not observed;

Glumes: Lanceolate; acute apex and truncate base; entire margin; navicular; glabrous; awnless; lower glume to about 3 mm long and about 1 mm across; upper glume to about 5 mm long and about 1 mm across;

Glume color: Adaxial and abaxial nearest RHS 158B;

Fragrance: None detected;

Lemma: Two; lanceolate; navicular; glaucous; about 4 mm long and about 1 mm across; color nearest RHS 158B;

Androecium: Protruding from lemma;

*Filaments*.—Thin, flexible; to about 2.5 mm long, exserted about 1 mm outside lemma, less than 0.1 mm in diameter; color nearest RHS NN155D.

*Anther*.—About 3.5 mm long and 1 mm across, versatile; color nearest RHS 8C.

*Pollen*.—Abundant on fertile anthers; color nearest RHS 8C.

Seeds have not yet been observed;

Hardiness: To at least U.S.D.A. zones 3 to 7;

Growth: The new plant is tolerate of poor soils including clay soils if good drainage is provided,. and resistant to drought once established;

Ploidy: Not verified scientifically, but presumed to be hexaploid;

Pest and disease resistance: No other susceptibility or resistance to diseases including *Fusarium* and *Rhizoctonia* or pests including *Odocoileus virginianus* and *Sylvilagus floridanus* have been observed except that which is common to blue fescue.

It is claimed:

1. A new and distinct *Festuca arundinacea* plant named 'Perfect Edging' as herein described and illustrated.

* * * * *